United States Patent [19]

Alig et al.

[11] Patent Number: 4,871,755
[45] Date of Patent: Oct. 3, 1989

[54] METHOD FOR TREATING DIABETES OBESITY AND CONDITIONS CHARACTERIZED BY INCREASED PROTEIN BREAKDOWN WITH NOVEL OXAZOLIDINES

[75] Inventors: Leo Alig, Kaiseraugst; Marcel Müller, Frenkendorf, both of Switzerland

[73] Assignee: Hoffmann-La Roche Inc., Nutley, N.J.

[21] Appl. No.: 152,522

[22] Filed: Feb. 5, 1988

Related U.S. Application Data

[62] Division of Ser. No. 667,186, Nov. 1, 1984, Pat. No. 4,743,604.

[30] Foreign Application Priority Data

Nov. 10, 1983 [CH] Switzerland ............ 6070/83
Sep. 20, 1984 [CH] Switzerland ............ 4499/84

[51] Int. Cl.$^4$ ............ A61K 31/42; A61K 31/495
[52] U.S. Cl. ............ 514/376; 514/252; 544/367; 548/229; 548/231; 548/232
[58] Field of Search ............ 544/367; 514/252, 376

[56] References Cited

U.S. PATENT DOCUMENTS 4,156,789 5/1979 Hauck et al. ............ 568/736

OTHER PUBLICATIONS

Ariens, E. S., *Drug Design*, Academic Press, N.Y. (1971) pp. 74, 92.
Burger Alfred, *Medicinal Chemistry III*, Wiley Interscience (1970) p. 71.
Derwent Abstract 15538.
Derwent Abstract 18335.
Derwent Abstract 20925.
Derwent Abstract 22707.
Derwent Abstract 26138.
Derwent Abstract 36501.
Derwent Abstract 36802.
Derwent Abstract 33331e.
Derwent Abstract 19557r.
Derwent Abstract 35794r.
Derwent Abstract 74007r.
Derwent Abstract 84541r.
Derwent Abstract 69076s.
Derwent Abstract 75837s.
Derwent Abstract 77515s.
Derwent Abstract 1836t.
Derwent Abstract 48801u.
Derwent Abstract 49596v.
Derwent Abstract 54111v.
Derwent Abstract 30464w.
Derwent Abstract 29125v.

*Primary Examiner*—Cecilia Shen
*Attorney, Agent, or Firm*—Jon S. Saxe; Bernard S. Leon; Matthew Boxer

[57] ABSTRACT

The oxazolidines of the formula

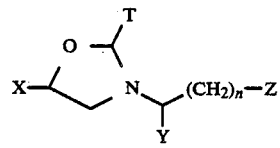

wherein
  n signifies the number 1 or 2.
  T signifies lower carbalkoxy.
  X signifies phenoxymethyl optionally mono-fluorinated or mono-chlorinated in the ortho-position or phenyl optionally monosubstituted by fluorine, chlorine, trifluoromethyl or lower-alkoxy.
  Y signifies hydrogen or methyl, and
  Z signifies a phenyl or thienyl residue substituted in a defined manner.

and the physiologically compatible salts thereof have catabolic activity and can be used for the treatment of obesity and diabetes mellitus or for the treatment of conditions which are associated with an increased protein breakdown, or as feed additives for fattening animals. They are manufactured starting from corresponding primary amines.

9 Claims, No Drawings

METHOD FOR TREATING DIABETES OBESITY AND CONDITIONS CHARACTERIZED BY INCREASED PROTEIN BREAKDOWN WITH NOVEL OXAZOLIDINES

This is a division of application Ser. No. 667,186 filed Nov. 1, 1984, now U.S. Pat. No. 4,743,604.

The present invention is concerned with novel oxazolidines, a process for their manufacture and pharmaceutical preparations based on these compounds.

The oxazolidines in accordance with the invention are compounds of the formula

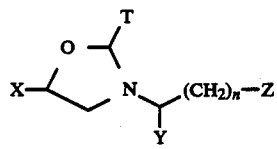

wherein
n is the number 1 or 2,
T is lower-carbalkoxy,
X is phenoxymethyl optionally mono-fluorinated or mono-chlorinated in the ortho-position or phenyl optionally monosubstituted by fluorine, chlorine, trifluoromethyl or lower-alkoxy,
Y is hydrogen or methyl,
Z is a group of the formula

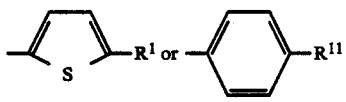

$R^1$ is lower-alkyl, optionally N-mono-lower-alkylated or N-di-lower-alkylated aminomethyl or a residue —C(O)$R^2$, —C($R^3$)=CH—(CH$_2$)$_m$—C(O)$R^2$, —C(H,$R^3$)—(CH$_2$)$_{m+1}$—C(O)$R^2$, —C(H,$R^3$)—(CH$_2$)$_p$—OH or —C($R^3$)=CH—C(CH$_3$)=CH—COOCH$_3$,
$R^{11}$ is hydroxy, lower-alkoxy, lower-alkanoyloxy, sulphamoyl, benzyloxy or phenoxy optionally ring-substituted by fluorine, chlorine, trifluoromethyl, lower-alkyl or lower-alkoxy, or a group $R^1$,

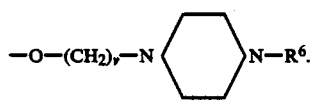

$R^2$ is hydroxy, lower-alkyl, lower-alkoxy, dimethylaminoethoxy, lower-alkoxycarbonylethyl or optionally mono-lower-alkylated or di-lower-alkylated amino.
$R^3$ is hydrogen or methyl,
$R^4$ is lower-alkyl,
$R^5$ is hydrogen, lower-alkyl or phenyl optionally para-substituted by chlorine, fluorine, trifluoromethyl, lower-alkyl or lower-alkoxy,
$R^6$ is lower-alkyl or phenyl optionally para-substituted by fluorine, chlorine, lower-alkyl or lower-alkoxy,
m and p are whole numbers of 0 to 6,
v is a whole number of 2 to 4,
q and t are whole numbers of 1 to 6, and physiologically compatible salts thereof.

The term "lower" used herein denotes residues with 1–6 carbon atoms, residues with 1–4 carbon atoms being preferred. Alkyl and alkoxy groups can be straight-chain or branched. Examples are methyl, ethyl, propyl, isopropyl, n-butyl and isobutyl and methoxy, ethoxy, propoxy, isopro-poxy, butoxy and isobutoxy, respectively. Lower-alkanoyloxy residues are derived from lower-alkanecarboxylic acids such as formic acid, acetic acid, propionic acid and butyric acid.

The compounds of formula I form acid addition salts with acids, which are likewise an object of the invention. Examples of such salts are salts with physiologically compatible mineral acids such as hydrochloric acid, hydrobromic acid, sulphuric acid, phosphoric acid; or with organic acids such as methanesulphonic acid, acetic acid, propionic acid, citric acid, oxalic acid, succinic acid, malic acid, fumaric acid, phenylacetic acid or salicylic acid. Carboxylic acids of formula I can exist as salts. Examples of such salts are alkali metal, alkaline earth metal, ammonium and alkylammonium salts such as Na, K, Ca, trimethylammonium and ethanolammonium salts.

The compounds of formula I contain at least two asymmetric carbon atoms and can therefore exist as optically active enantiomers, as diastereomers or as racemates.

The compounds of formula I can be obtained in accordance with the invention by reacting an amine of the formula

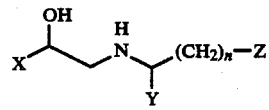

wherein n, X, Y and Z have the significance given above, with a compound of the formula TCHO, wherein T is lower-carbalkoxy, and, if desired, converting a compound of formula I obtained into a salt.

The reaction of an amine of formula II with a compound of the formula TCHO is conveniently carried out in a solvent, preferably an aromatic hydrocarbon such as benzene or toluene, and at room temperature or at elevated temperature, preferably by azeotropic distillation of the reaction mixture.

The compounds of formula II can be obtained by
(a) reacting an epoxide of the formula

or a β-keto halide of the formula

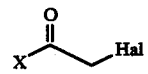

with an amine of the formula

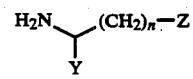

and reducing a —C(O)— group present in a compound obtained to a —CHOH— group, or (b) reducing a compound of one of the formulae

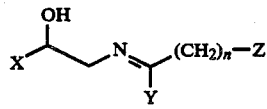  V

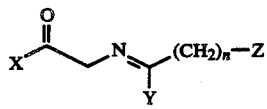  VI

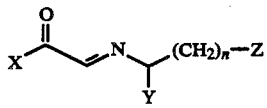  VII

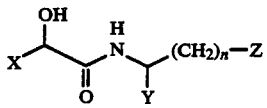  VIII

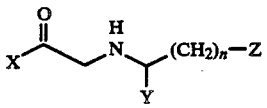  IX and (c) if desired, functionally modifying reactive substituents present in a group Z of a compound of formula II.

The reaction of a compound of formula II-1 or III-1 with a compound of formula IV can be carried out in an inert organic solvent, conveniently a protic solvent such as a lower alkanol, e.g. ethanol. The reaction temperature is not critical, it can lie between room temperature and the reflux temperature of the reaction mixture.

The reduction of a compound of formula V can be carried out by catalytic hydrogenation, e.g. in the presence of noble metal catalysts such as Pd or Pt catalysts, or by treatment with a complex metal hydride such as NaBH$_4$. The reaction conditions which are usually used for such reductions can be used in this case. The catalytic hydrogenation is conveniently carried out in an inert organic solvent such as a lower alkanol, e.g. ethanol, at room temperature or a slightly elevated temperature, e.g. at 20°–80° C. The reduction with a complex metal hydride is conveniently carried out in a lower alkanol, e.g. methanol, at temperatures of 20°–30° C.

The compounds of formulae VI to IX can be reduced with a complex metal hydride in analogy to the compounds of formula V. NaBH$_4$ is a suitable complex metal hydride for the reduction of the compounds VI and VII. The compounds VIII are conveniently reduced with LiAlH$_4$.

A keto group X—C(O)— which results in the reaction of a compound III-2 with a compound IV can be reduced in a manner known per se to the secondary alcohol group. This reduction can be carried out under the same conditions as for the reduction of the compounds V–IX described above, whereby the reduction with a complex metal hydride, especially NaBH$_4$, is preferred because of its selectivity.

A reactive substituent, especially a group —C(O)R$^2$ or —C(R$^3$)=CH—(CH$_2$)$_m$—C(O)R$^2$, in the thus-obtained reaction product of formula II can be functionally modified. The esterification of a carboxyl group can be carried out in a manner known per se, e.g. by means of alkyl halides such as methyl iodide and a base. The saponification of an ester group is conveniently carried out under alkaline conditions, e.g. by means of aqueous-alcoholic alkali hydroxide, e.g. aqueous-methanolic potassium hydroxide. A double bond present in a side-chain R$^1$ or R$^{11}$ can be hydrogenated to a single bond e.g. in the presence of a catalyst such as palladium-on-carbon in a solvent such as a lower alkanol, e.g. ethanol. A hydroxy residue R$^{11}$ can be etherified in a manner known per se, e.g. by reaction with a mesylate or halide corresponding to the ether residue and in the presence of a base such as potassium hydroxide in a solvent such as a lower alkanol, e.g. n-propanol, or in the presence of potassium t-butylate in a solvent such as DMSO.

An optionally mono-lower alkylated or di-lower alkylated carbamoyl group R$^1$ or R$^{11}$ can be reduced to the corresponding aminomethyl group by reduction e.g. with complex metal hydrides such as LiAlH$_4$. A lower-alkoxycarbonyl group can be reduced to the hydroxymethyl group in an analogous manner.

The compounds of formulae V—IX can be prepared in a manner known per se, e.g. the compounds of formula VIII can be prepared by reacting an acid of the formula X$^1$—C(H,OH)—COOH with an amine of formula IV.

Preferred compounds of formula I are those in which the substituent R$^{11}$ present on a phenyl group Z is hydroxy, lower alkoxy, lower-alkanoyloxy, sulphamoyl or a group R$^1$, —O—(CH$_2$)$_q$—OH, —O—(CH$_2$)$_q$—COOR$^4$, —O—(CH$_2$)$_q$—O—(CH$_2$)$_r$—R$^5$ and R$^5$ is hydrogen, lower-alkyl or phenyl.

Preferred compounds of formula I are, further, those in which T is carbomethoxy.

Preferred compounds of formula I are, further, those in which X is phenyl monosubstituted by chlorine or trifluoromethyl in the meta-position, or phenoxymethyl, especially those in which the C-atom bonded to a phenoxymethyl residue X has the S-configuration or the C-atom bonded to a phenyl residue X has the R-configuration.

Furthermore, there are preferred those compounds of formula I in which Y is methyl, especially those in which the C-atom bonded to a methyl residue Y has the R-configuration.

Furthermore, there are preferred those compounds of formula I in which Z is phenyl or thienyl substituted by carbamoyl, methoxycarbonyl or 2-(ethoxy or methoxy)-carbonyl-1-methylvinyl.

Furthermore, there are preferred those compounds of formula I in which Z is p-hydroxyphenyl or phenyl substituted by 6-hydroxyhexoxy, 2-ethoxyethoxy, 2-phenethoxy-2-ethoxy or (ethoxy or methoxy)-carbonylmethoxy.

Especially preferred compounds of formula I are those in which T is carbomethoxy, X is phenyl monosubstituted by chlorine or trifluoromethyl in the meta-position, or phenoxymethyl, Y is methyl and Z is p-hydroxyphenyl or phenyl or thienyl substituted by carbamoyl, methoxycarbonyl or 2-(ethoxy or methoxy)-carbonyl-1-methylvinyl, or phenyl substituted by 6-hydroxyhexoxy, 2-ethoxyethoxy, 2-phenethoxy-2-ethoxy or (ethoxy or methoxy)-carbonylmethoxy.

Furthermore, especially preferred compounds of formula I are those in which the C-atom bonded to a methyl residue Y has the R-configuration, the C-atom bonded to a phenoxymethyl residue X has the S-configuration and the C-atom bonded to a phenyl residue X has the R configuration.

Examples of preferred compounds of formula I are:

methyl(2RS,5R)-3-[(RS)-4-(5-carbamoyl-2-thienyl)-2-butyl-5-phenyl-2-oxazolidinecarboxylate, methyl(2RS,5R)-3-[(R)-3-(p-carbamoylphenyl)-1-methylpropyl]-5-phenyl-2-oxazolidinecarboxylate and particularly methyl(E)-p-[(R)-2-[(2RS,5RS)-2-methoxycarbonyl)-5-(α,α,α-trifluoro-m-tolyl)-3-oxazolidinyl]propyl]-β-methyl-cinnamate and methyl(2RS,5R)-3-[(R)-3-(p-carbamoylphenyl)-1-methylpropyl]-5-phenoxymethyl-2-oxazolidinecarboxylate.

The oxazolidines of formula I as well as the physiologically compatible salts thereof can be used as active substances in pharmaceutical preparations for the treatment of obesity and/or diabetes mellitus, especially in obese adult diabetics. In an animal experiment an increased catabolism, primarily of fat, has been observed upon the administration of the above compounds. Furthermore, it has been observed that the compounds stimulate the formation of brown adipose tissue in rats and obese-hyperglycaemic mice. It is known that defects of the brown adipose tissue play a substantial role in the origin of obesity. In obese-hyperglycaemic mice the compounds have a pronounced antidiabetic effect, in that they have hypoglycaemic activity and reduce glycosuria. These compounds exhibit only a slight activity on the working of the heart and circulation. The dosage can amount to 0.5-1000 mg, preferably 2-200 mg, per day for an adult depending on the strength of activity of the individual compounds and on the individual requirements of the patients, whereby the dosage can be administered as a single dosage or in several dosages divided over the day.

In addition, in an animal experiment with the above compounds an increase in the body protein content and a decrease in the fat content could be detected. These compounds therefore lead to an increase in the lean composition of the body at the expense of fat. Accordingly, they can be used above all in human medicine for the treatment of conditions which are associated with high protein breakdown, e.g. in convalescene after an operation. In this case the dosages administered lie in the same range as in the treatment of obesity and/or of diabetes mellitus.

The above compounds can also be used in the maintenance of fattening animals such as beef cattle, pigs, sheep and poultry. In this case the dosages administered and the dosage forms administered can be the same as in the case of vitamins. These compounds can also be used as feed additives in dosages of 0.01-100 mg/kg depending on the substance, kind of animal and age.

The pharmaceutical preparations contain the active substance together with a compatible pharmaceutical organic or inorganic carrier material such as e.g. water, gelatine, gum arabic, lactose, starch, magnesium stearate, talc, vegetable oils, polyalkylene glycols, Vaseline and the like. The pharmaceutical preparations are preferably administered orally, e.g. in the form of tablets, capsules, pills, powders, granulates, solutions, syrups, suspensions, elixirs and the like. The administration can, however, also be carried out parenterally, e.g. in the form of sterile solutions, suspensions or emulsions. The pharmaceutical preparations can be sterilized and/or can contain ingredients such as preserving agents, stabilizers, wetting agents, emulsifiers, salts for varying the osmotic pressure and buffer substances.

The activity of the above compounds is evident from the following test results:

(1) Activity on oxygen consumption

Male albino rats weighing 160-180 g were placed in metabolic cages after fasting for 24 hours. The cages were ventilated with a constant 6 liter room air/minute which was equilibrated at a dew point of 11° C. Samples of the spent air were collected during periods of in each case 14 minutes after again equilibrating and the oxygen content and $CO_2$ content were analyzed. After an adaptation time of 4 hours the animals, divided into groups of 6, received either placebo (5% gum arabic) or the test substance (suspended in 5% gum arabic) per os. Thereafter, the determinations were carried out for a period of 12 hours. In Table I there is given the percentage of the average oxygen consumption after medication during the first 3 hours and the entire test duration (12 hours) of the oxygen consumption of the adaptation period, corresponding corrections for variations in the placebo group having been taken into consideration.

TABLE I

| Compound prepared in Example No. | Dosage μ/kg | $O_2$ consumption of the of the value of the pre-period | |
|---|---|---|---|
| | | 1st-3rd hour | 1st-12th hour |
| 1 | 1 | 135 | 110 |
| 2 | 30 | 148 | 113 |
| 3 | 30 | 143 | 113 |
| 4a | 3 | 133 | 111 |
| 4b | 10 | 161 | 121 |
| 4c | 3 | 147 | 133 |
| 4d | 1 | 131 | 113 |
| 4e | 10 | 147 | 123 |
| 4f | 10 | 154 | 117 |
| 4g | 100 | 137 | 112 |
| 4h | 30 | 125 | 111 |
| 4i | 30 | 153 | 121 |

(2) Catabolic activity on lipids

Groups of 4 male albino rats weighing 320-360 g were kept in metabolic cages without access to feed. Oxygen consumption and $CO_2$ production were measured during 12 hours. After 4 hours the animals received placebo (5% gum arabic) or the test substance (suspended in gum arabic) per os. In Table II there is given the average decrease of the respiratory quotient ($CO_2/O_2$) during 8 hours after administration of the test substance in comparison to the last 3 hours before administration of the test substance. Variations appearing in the placebo group were taken into consideration in the calculation.

TABLE II

| Compound prepared in Example No. | Dosage μM/kg | Variation of the respiratory quotient |
|---|---|---|
| (4c) | 10 | −0.035 |

(3) Activity on urine glucose and blood glucose and the formation of brown adipose tissue Female hyperglycaemic fat mice were adapted to an amount of feed limited to 3 g/day/animal. The test compounds (suspended in 5% gum arabic) or placebo (5% gum arabic) were administered orally twice daily during 15 days. Urine was collected for 6 days a week and urine glucose was determined. Blood glucose and the weight of the interscapular brown adipose tissue were determined at the end of the test.

The test results are given in Table III as a percentage of the control value.

TABLE III

| Compound prepared in Example No. | Dosage μM/kg per day | Urine glucose 1st week/ | Urine glucose 2nd week | Blood glucose | Brown adipose tissue |
| --- | --- | --- | --- | --- | --- |
| (4c) | 60 | 11% | 0% | 24% | 217% |

The amine starting materials used in the following Examples, especially the amines of formula II in which X is phenyl optionally monosubstituted by fluorine, chlorine, trifluoromethyl or lower-alkoxy and the amines of formula IV, are known or can be prepared in a manner known per se, e.g. as described in European Patent Applications 6735, 21636 and 94595.

For the preparation of the amine starting material of Examples 4(h) a mixture of 3.8 g of S-1-methyl-3-(4-amino-carbonylphenyl)propylamine and 3.60 g of 2,3-epoxypropyl phenyl ether in 30 ml of ethanol and 20 ml of acetonitrile was heated under reflux for 8 hours. The reaction solution was evaporated in vacuo and the residue was chromatographed on 250 g of silica gel. 2.4 g of amorphous p-[(S)-3-[bis-[(RS)-2-hydroxyphenoxypropyl]amino]butyl]benzamide were firstly eluted with the mixture chloroform/n-propanol/25% NH$_3$ (1000:50:5). With the mixture chloroform/n-propanol/25% NH$_3$ (100:10:1) there were subsequently eluted 3.5 g of pure p-[(S)-3-[[(RS)-2-hydroxy-3-phenoxypropyl]amino]butyl]benzamide, m.p. 133°–136° (from acetonitrile), $[\alpha]_D^{20}=-2°$ (c=0.8 in methanol). $\epsilon_{223}=15510$, $\epsilon_{236}=13820$.

The amine starting materials of Examples 4(e) and 4(i) were manufactured analogously thereto:

p-[(R)-3-[[(RS)-2-Hydroxy-3-phenoxypropyl]amino]butyl]benzmide, m.p. 132°–136° (acetonitrile), $[\alpha]_D^{20}=+2°$ (c=1.0 in methanol), $\epsilon_{222}=15250$, $\epsilon_{236}=13630$; and (RS)-p-[3-[(2-hydroxy-3-phenoxypropyl)amino]propyl]benzamide, m.p. 121°–122° (acetone), $\epsilon_{222}=15170$, $\epsilon_{235}=13540$.

The following Examples illustrate the invention in more detail.

EXAMPLE 1

1.91 g of 5-[(RS)-3-[[(R)-β-hydroxyphenethyl]amino]butyl]-2-thiophenecarboxamide and 0.8 g of methyl glyoxylate were stirred at 25° C. for 5 hours in 60 ml of benzene. The reaction mixture was diluted with MeOH and ethyl acetate and washed with water, dried over sodium sulphate and evaporated in vacuo. Chromatography of the residue on silica gel with methylene chloride-ether gave 1 g of methyl(2RS,5R)-3-[(RS)-4-(5-carbamoyl-2-thienyl)-2-butyl-5-phenyl-2-oxazolidinecarboxylate, $[\alpha]_D=-41°$ (0.1% in dioxan); $\epsilon_{277}=10400$, $\epsilon_{258}=8000$.

EXAMPLE 2

1.91 g of methyl 5-[3-[[(R)-β-hydroxyphenethyl]amino]propyl]-2-thiophenecarboxylate and 1.05 g of methyl glyoxylate were heated to reflux in 20 ml of toluene for 1 hour on a water separator. The reaction mixture was diluted with ethyl acetate and washed with water. The ethyl acetate solutions were dried and evaporated in vacuo. Chromatography of the residue on silica gel gave 1.5 g of methyl(2RS,5R)-3-[3-(5-carbomethoxy-2-thienyl)propyl]-5-phenyl-2-oxazolidinecarboxylate, $[\alpha]_D=-12°$ (0.1% in dioxan); $\epsilon_{278}=12300$, $\epsilon_{255}=9300$.

EXAMPLE 3

In analogy to Example 1 there was prepared methyl(2RS,5R)-3-[2-(5-carbamoyl-2-thienyl)ethyl]-5-phenyl-2-oxazolidinecarboxylate, $[\alpha]_D=-12°$ (c=0.1% in dioxan), $\epsilon_{258}=8840$, $\epsilon_{275}$ 10660.

EXAMPLE 4

In a manner analogous to Example 2 there were prepared:
(a) Methyl 3-[3-(p-carbamoylphenyl)propyl]-5-phenyl-2-oxazolidinecarboxylate, m.p. 142°–144° (acetone-hexane), $[\alpha]_D^{20}=+17°$ (c=0.3 in methanol), $\epsilon_{236}=14520$;
(b) methyl(2RS,5R)-3-[(S)-3-(carbamoylphenyl)-1-methylpropyl]-5-phenyl-2-oxazolidinecarboxylate, amorphous, $[\alpha]_D^{20}=+6°$ (c=0.4 in methanol), $\epsilon_{236}=14150$;
(c) methyl(E)-p-[(R)-2-[(2RS,5RS)-2-methoxycarbonyl)-5-(α,α,α-trifluoro-m-tolyl)-3-oxazolidinyl]]propyl]-β-methyl-cinnamate, amorphous, $[\alpha]_D^{20}=-28°$ (c=0.5 in methanol), $\epsilon_{271}=14800$;
(d) methyl(2RS,5R)-3-[(R)-3-(p-carbamoylphenyl)-1-methylpropyl]-5-phenyl-2-oxazolidinecarboxylate, amorphous, $[\alpha]_D^{20}=-67°$ (c=1.0 in methanol), $\epsilon_{236}=13600$;
(e) methyl(2RS,5R)-3-[(R)-3-(p-carbamoylphenyl)-1-methylpropyl]-5-phenoxymethyl-2-oxazolidinecarboxylate, amorphous, $[\alpha]_D^{20}=-13°$ (c=0.6 in methanol), $\epsilon_{222}=14730$, $\epsilon_{237}=13540$;
(f) methyl(2RS,5R)-3-[(S)-p-carbamoyl-α-methylphenethyl]-5-phenyl-2-oxazolidinecarboxylate, amorphous, $[\alpha]_D^{20}=+40°$ (c=0.4 in methanol), $\epsilon_{234}=14000$;
(g) methyl(2RS,5R)-3-[(S)-3-(p-hydroxyphenyl)-1-methylpropyl]-5-phenyl-2-oxazolidinecarboxylate, amorphous, $[\alpha]_D^{20}=+11°$ (c=0.9 in methanol), $\epsilon_{224}=11000$;
(h) methyl(2RS,5RS)-3-[(S)-3-(p-carbamoylphenyl)-1-methylpropyl]-5-(phenoxymethyl)-2-oxazolidinecarboxylate, amorphous, $[\alpha]_D^{20}=+12°$ (c=0.5 in methanol), $\epsilon_{222}=13640$, $\epsilon_{238}=13000$;
(i) methyl(2RS,5RS)-3-[3-(p-carbamoylphenyl)propyl]-5-phenoxymethyl-2-oxazolidinecarboxylate, amorphous, $\epsilon_{222}=14900$, $\epsilon_{236}=13550$.

EXAMPLE 5

In analogy to Example 1, starting from methyl glyoxylate and (RS)-1-[[3-[5-[(dibutylamino)methyl]-2-thienyl]propyl]amino]-3-phenoxy-2-propanol there was obtained methyl(2RS,5RS)-3-[3-[5-[(dibutylamino)methyl]-2-thienyl]propyl]-5-phenoxymethyl-2-oxazolidinecarboxylate, $\epsilon_{220}=12900$, $\epsilon_{240}=9520$, $\epsilon_{270}=1930$, $\epsilon_{277}=1500$.

The propanolamine starting material can be prepared as follows:

(a) 2-(p-Toluenesulphonyloxy)-propylthiophene was reacted with acetyl chloride and aluminium trichloride in methylene chloride to give 5-acetyl-2-(p-toluenesulphonyloxy)-propylthiophene. With sodium azide in DMSO there was obtained therefrom 5-(3-azidopropyl)-2-thienyl methyl ketone. Oxidation with sodium hypobromite gave 5-(3-azidopropyl)-2-thiophenecarboxylic acid, m.p. 71°–72°. Reaction of this acid with thionyl chloride and subsequent treatment with conc. ammonia yielded 5-(3-azidopropyl)-2-thiophenecarboxamide, m.p. 85°-87°. There was obtained therefrom after treatment with triphenylphosphine and hydrolysis 5-(3-aminopropyl)-2-thiophenecarboxamide, m.p. 143.5°-144° (from water).

(b) Via 5-[3-(2,5-dimethylpyrrol-1-yl)propyl]-2-thiophenecarboxamide, m.p. 144°-146° C. and by reaction with n-butyl bromide, the product of (a) was butylated to 5-(3-aminopropyl-N,N-dibutyl-2-thiophenecarboxamide, $\epsilon_{245}=8610$, $\epsilon_{273}=8310$.

(c) The product of (b) was reacted with 2,3-epoxypropyl phenyl ether in DMSO at 90° C. to give 5-[3-[[(RS)-2-hydroxy-3-phenoxypropyl]amino]propyl]-N,N-dibutyl-2-thiophenecarboxamide, $\epsilon_{219}=13150$, $\epsilon_{244}=9260$, $\epsilon_{270}=10240$, $\epsilon_{276}=9960$.

(d) The product of (c) was reacted with LiAlH$_4$ in THF at room temperature to give (RS)-1-[[3-[5-[(dibutylamino)methyl]-2-thienyl]propyl]amino]-3-phenoxy-2-propanol, $\epsilon_{220}=13050$, $\epsilon_{240}=9350$, $\epsilon_{270}=1950$, $\epsilon_{277}=1560$.

EXAMPLE 6

387 mg of (RS)-1-[[(R)-3-[α-(butylamino)-p-tolyl]-1-methylpropyl]amino]-3-phenoxy-2-propanol, 102 mg of methyl glyoxylate and 195 mg of p-toluenesulfonic acid monohydrate in 5 ml of benzene were stirred at 20°-25° C. for 6 hours. The mixture was worked up with ether and sodium bicarbonate solution. Chromatography of the crude product on silica gel with ether-methanol gave methyl(2RS,5RS)-3-[(R)-3-[α-(butylamino)-p-tolyl]-1-methylpropyl]-5-phenoxymethyl-2-oxazolidinecarboxylate, $[\alpha]_D=-9°$ (c=0.1 in methanol); $\epsilon_{219}=18140$, $\epsilon_{270}=1830$, $\epsilon_{277}=1430$.

The propanolamine starting material can be prepared as follows:

(a) Via p-[(R)-3-(2,5-dimethylpyrrol-1-yl)butyl]benzamide, p-[(R)-3-aminobutyl]benzamide was butylated to p-[(R)-3-aminobutyl]-N-butylbenzamide, $[\alpha]_D=+4°$ (0.1% in methanol).

(b) The product of (a) was reacted at 90° C. with 2,3-epoxypropyl phenyl ether in DMSO to give p-[(R)-3-[[(RS)-2-hydroxy-3-phenoxypropyl]amino]butyl]-N-butylbenzamide, $[\alpha]_D=+5°$ (0.1% in methanol)

(c) 2.1 g of p-[[(R)-3-[(RS)-2-hydroxy-3-phenoxypropyl]amino]butyl-N-butylbenzamide in 92 ml of THF were treated portionwise with 920 mg of LiAlH$_4$ and boiled at reflux for 4 hours. The reaction mixture was decomposed with 25 ml of 2N NaOH, diluted with water and extracted three times with methylene chloride. The methylene chloride solutions were washed with water, dried and evaporated in vacuo. There were obtained 2.06 g of (RS)-1-[[(R)-3-[α-(butylamino)-p-tolyl]-1-methylpropyl]amino]-3-phenoxy-2-propanol, $[\alpha]_{365}-+6°$ (0.1% in MeOH).

EXAMPLE 7

In analogy to the foregoing Examples, there were prepared:

Methyl(R)-3-[(R)-p-(methoxycarbonyl)-α-methylphenethyl[-5-phenyl-2-oxazolidinecarboxylate, amorph, $[\alpha]_D^{20°}=-47°$ (c=0.25 in MeOH)

methyl(S)-3-[(R)-p-hydroxy-α-methylphenethyl]-5-(phenoxymethyl)-2-oxazolidinecarboxylate, amorph, $[\alpha]_D^{20°}=-23°$ (c=0.2 in MeOH)

methyl(R)-3-[3-[p-(methoxycarbonyl)phenyl]propyl]-5-phenyl-2-oxazolidinecarboxylate, amorph, $[\alpha]_D^{20°}=-21°$ (c=0.3 in MeOH)

methyl(RS)-3-[3-[p-(methoxycarbonyl)phenyl]propyl]-5-(α,α,α-trifluoro-m-tolyl)-2-oxazolidinecarboxylate, amorph, methyl(R)-3-[(R)-p-acetyl-α-methylphenethyl]-5-phenyl-2-oxazolidinecarboxylate, amorph, $[\alpha]_D^{20°}=-79°$ (c=0.5 in MeOH)

methyl(R)-3-[(S)-3-[p-(dimethylcarbamoyl)phenyl]-1-methylpropyl]-5-phenyl-2-oxazolidinecarboxylate, amorph, $[\alpha]_D^{20°}=-42°$ (c=0.3 in MeOH).

EXAMPLE 8

Tablets of the following composition are manufactured in the usual manner:

| | |
|---|---|
| Active substance. e.g. methyl (E)—p-[(R)—2-[(2RS,5RS)—2-methoxycarbonyl-5-(trifluoro-m-tolyl)-3-oxazolidinyl]propyl]-β-methyl-cinnamate or p-[(S)—3-methyl-3-[(R)—5-phenyl-3-oxazolidinyl]propyl]benzamide | 250 mg |
| Lactose | 200 mg |
| Maize starch | 300 mg |
| Maize starch paste | 50 mg |
| Calcium stearate | 5 mg |
| Dicalcium phosphate | 45 mg |

We claim:

1. A method of treating disease conditions characterized by an increased protein breakdown, which method comprises administering a pharmaceutically effective amount of a compound of the formula

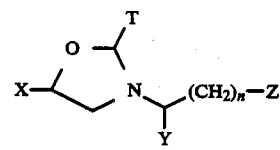

wherein
n is the number 1 or 2,
T is lower-carbalkoxy,
X is phenoxymethyl optionally mono-fluorinated or mono-chlorinated in the ortho-position or phenyl optionally monosubstituted by fluorine, chlorine, trifluoromethyl or lower-alkoxy,
Y is hydrogen or methyl,
Z is a group of the formula

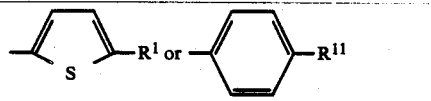

R$^1$ is lower-alkyl, optionally N-mono-lower-alkylated or N-di-lower-alkylated aminomethyl or a residue —C(O)R$^2$, —C(R$^3$)=CH—(CH$_2$)$_m$—C(O)R$^2$, —C(H,R$^3$)—(CH$_2$)$_{m+1}$—C(O)R$^2$, —C(H,R$^3$)—(CH$_2$)$_p$—OH or —C(R$^3$)=CH—C(CH$_3$)=CH—COOCH$_3$, R$^{11}$ is hydroxy, lower-alkoxy, lower-alkanoyloxy, sulphamoyl, benzyloxy or phenoxy or a group R$^1$, —O—(CH$_2$)$_q$—OH, —O—(CH$_2$)$_q$—COOR$^4$—O—(CH$_2$)$_q$—O—(CH$_2$)$_k$—R$^5$ or,

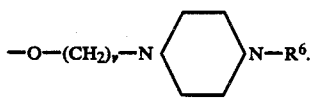

R² is hydroxy, lower-alkyl, lower-alkoxy, dimethylaminoethoxy, lower-alkoxycarbonylethyl or optionally mono-lower-alkylated or di-lower-alkylated amino, R³ is hydrogen or methyl, R⁴ is lower-alkyl, R⁵ is hydrogen, lower-alkyl or phenyl optionally para-substituted by chlorine, fluorine, trifluoromethyl, lower-alkyl or lower-alkoxy, R⁶ is lower-alkyl or phenyl optionally para-substituted by fluorine, chlorine, lower-alkyl or lower-alkoxy, m and p are whole numbers of 0 to 6, v is a whole number of 2 to 4, q and t are whole numbers of 1 to 6, or a physiologically compatible salt thereof.

2. A method of treating diabetes which method comprises administering an effective amount of a compound of formula

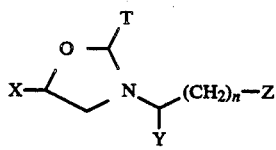

wherein n is the number 1 or 2,

T is lower-carbalkoxy,

X is phenoxymethyl optionally mono-fluorinated or mono-chlorinated in the ortho-position or phenyl optionally monosubstituted by fluorine, chlorine, trifluoromethyl or lower-alkoxy, Y is hydrogen or methyl, Z is a group of the formula

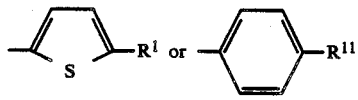

R¹ is lower-alkyl, optionally N-mono-lower-alkylated or N-di-lower-alkylated aminomethyl or a residue —C(O)R², —C(R³)=CH—(CH₂)m—C(O)R², —C(H,R³)—(CH₂)$_{m+1}$—C(O)R², —C(H,R³)—(CH₂)p—OH or —C(R³)=CH—C(CH₃)=CH—COOCH₃, R¹¹ is hydroxy, lower-alkoxy, lower-alkanoyloxy, sulphamoyl, benzyloxy or phenoxy or a group R¹, —O—(CH₂)$_q$OH, —O—(CH₂)$_q$—COOR⁴ —O—(CH₂)$_q$—O—(CH₂)$_r$—R⁵ or

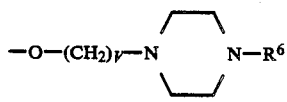

R² is hydroxy, lower-alkyl, lower-alkoxy, dimethylaminoethoxy, lower-alkoxycarbonylethyl or optionally mono-lower-alkylated or di-lower-alkylated amino, R³ is hydrogen or methyl, R⁴ is lower-alkyl, R⁵ is hydrogen, lower-alkyl or phenyl optionally para-substituted by chlorine, fluorine, trifluoromethyl, lower-alkyl or lower-alkoxy, R⁶ is lower-alkyl or phenyl optionally para-substituted by fluorine, chlorine, lower-alkyl or lower-alkoxy, m and p are whole numbers of 0 to 6, v is a whole number of 2 to 4, q and t are whole numbers of 1 to 6, or a physiologically compatible salt thereof.

3. A method of treating obesity which method comprises administering an effective amount of a compound of formula

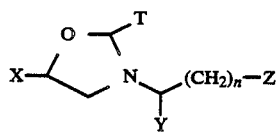

wherein n is the number 1 or 2,

T is lower-carbalkoxy,

X is phenoxymethyl optionally mono-fluorinated or mono-chlorinated in the ortho-position or phenyl optionally monosubstituted by fluorine, chlorine, trifluoromethyl or lower-alkoxy, Y is hydrogen or methyl, Z is a group of the formula

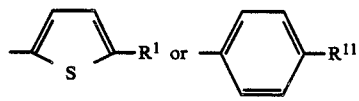

R¹ is lower-alkyl, optionally N-amino-lower-alkylated or N-di-lower-alkylated aminomethyl or a residue —C(O)R², —C(R³)=CH—(CH₂)m—C(O)R², —C(H,R³)—(CH₂)$_{m+1}$—C(O)R², —C(H,R³)—(CH₂)p—OH or —C(R³)=CH—C(CH₃)=CH—COOCH₃, R¹¹ is hydroxy, lower-alkoxy, lower-alkanoyloxy, sulphamoyl, benzyloxy or phenoxy or a group R¹, —O—(CH₂)$_q$OH, —O—(CH₂)$_q$—COOR⁴ —O—(CH₂)$_q$—O—(CH₂)$_r$—R⁵ or

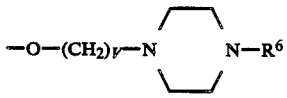

R² is hydroxy, lower-alkoxy, lower-alkoxy, dimethylaminoethoxy, lower-alkoxycarbonylethyl or optionally mono-lower-alkylated or di-lower-alkylated amino, R³ is hydrogen or methyl, R⁴ is lower-alkyl, R⁵ is hydrogen, lower-alkyl or phenyl optionally para-substituted by chlorine, fluorine, trifluoromethyl, lower-alkyl or lower-alkoxy, R⁶ is lower-alkyl or phenyl optionally para-substituted by fluorine, chlorine, lower-alkyl or lower-alkoxy, m and p are whole numbers of 0 to 6, v is a whole number of 2 to 4, q and t are whole numbers of 1 to 6, or a physiologically compatible salt thereof.

4. A method in accordance with claim 1 wherein T is carbomethoxy.

5. A method in accordance with claim 4, wherein the compound of formula I is methyl(E)-p-[(R)-2-[(2RS,5RS)-2-methoxycarbonyl)-5-($\alpha,\alpha,\alpha$-trifluoro-m-tolyl-3-oxazolidinyl]propyl]-$\beta$-methyl-cinnamate.

6. A method in accordance with claim 2 wherein T is carboxymethoxy.

7. A method in accordance with claim 6 wherein the compound of formula I is methyl(E)-p-[(R)-[(2RS,5RS)-2-methoxycarbonyl)-5-($\alpha,\alpha,\alpha$-trifluoro-m-tolyl-3-oxazolidinyl]propyl]-$\beta$-methyl-cinnamate.

8. A method in accordance with claim 3 wherein T is carbomethoxy.

9. A method in accordance with claim 8, wherein the compound of formula I is methyl(E)-p-[(R)-[(2RS,5RS)-2-methoxy-carbonyl)-5-($\alpha,\alpha,\alpha$-trifluoro-m-tolyl-3-oxazolidinyl]propyl]-$\beta$-methyl-cinnamate.

* * * * *